(12) United States Patent
Wiegand et al.

(10) Patent No.: US 12,708,303 B2
(45) Date of Patent: Aug. 18, 2026

(54) APPARATUS FOR MEASURING A FLOW OF A FLUID, IN PARTICULAR A URINE FLOW

(71) Applicant: SONOTEC GmbH, Halle (DE)

(72) Inventors: Stefan Wiegand, Halle (DE); Hans-Joachim Münch, Halle (DE); Hans-Christian Schaich, Leipzig (DE); Maik Christl, Kabelsketal (DE); Nicki Bader, Halle (DE); Wolfgang Kircher, Halle (DE); Felix Kaczmarek, Halle (DE); Thomas Spangenberg, Halle (DE)

(73) Assignees: SONOTEC GMBH, Halle (DE); STEFAN WIEGAND, Halle (DE)

( * ) Notice: Subject to any disclaimer, the term of this patent is extended or adjusted under 35 U.S.C. 154(b) by 179 days.

(21) Appl. No.: 18/475,140

(22) Filed: Sep. 26, 2023

(65) Prior Publication Data

US 2024/0099626 A1 Mar. 28, 2024

(30) Foreign Application Priority Data

Sep. 26, 2022 (DE) ..................... 10 2022 124 611.6

(51) Int. Cl.
*A61B 5/20* (2006.01)
*A61B 5/00* (2006.01)

(52) U.S. Cl.
CPC ............ *A61B 5/208* (2013.01); *A61B 5/6887* (2013.01)

(58) Field of Classification Search
None
See application file for complete search history.

(56) References Cited

U.S. PATENT DOCUMENTS

| | | | | |
|---|---|---|---|---|
| 4,099,412 | A | 7/1978 | Nehrbass | |
| 4,891,993 | A | 1/1990 | Barker | |
| 5,046,510 | A * | 9/1991 | Ams | A61B 5/208 600/584 |
| 5,179,862 | A | 1/1993 | Lynnworth | |
| 5,596,948 | A | 1/1997 | Ritchie | |
| 11,274,952 | B2 | 3/2022 | Bober et al. | |
| 2007/0186337 | A1 | 8/2007 | Emr | |
| 2011/0046514 | A1* | 2/2011 | Greenwald | G01F 1/662 702/45 |

FOREIGN PATENT DOCUMENTS

| | | | | |
|---|---|---|---|---|
| DE | 3007855 | A1 | 9/1981 | |
| DE | 19613306 | A1 | 10/1996 | |
| DE | 69601544 | T2 | 9/1999 | |
| EP | 2564778 | A2 | 3/2013 | |
| GB | 2437549 | A | 10/2007 | |
| TW | 201224254 | A | 6/2012 | |
| WO | WO-2020048576 | A1 * | 3/2020 | A61B 5/208 |

OTHER PUBLICATIONS

Translation of DE 3007855 A1 (Year: 1982).*

* cited by examiner

*Primary Examiner* — Jay B Shah
(74) *Attorney, Agent, or Firm* — McCoy Russell LLP

(57) ABSTRACT

The invention relates to an apparatus for measuring a flow of a fluid in dependence on time, in particular a urine flow, including
- an intake funnel;
- a hose;
- an ultrasonic flow sensor;
- an overflow.

The apparatus is characterized in that
- a first end of the hose is connected to the intake funnel and a second end of the hose is connected to the overflow;
- the ultrasonic flow sensor is arranged on the hose;
- the hose is U-shaped.

10 Claims, 6 Drawing Sheets

APPARATUS FOR MEASURING A FLOW OF A FLUID, IN PARTICULAR A URINE FLOW

CROSS REFERENCE TO THE RELATED APPLICATION

The present application claims priority to German Patent Application No. 10 2022 124 611.6 filed on Sep. 26, 2022. The entire contents of the above-listed application are hereby incorporated by reference for all purposes.

TECHNICAL FIELD

The disclosure relates to an apparatus for measuring a flow of a fluid in dependence on time, in particular a urine flow, comprising an intake funnel;

a hose;

an ultrasonic flow sensor;

an overflow.

The apparatus is characterized in that a first end of the hose is connected to the intake funnel and a second end of the hose is connected to the overflow;

the ultrasonic flow sensor is arranged on the hose;

the hose is U-shaped.

BACKGROUND

In particular in urology, this is used especially for diagnosing urinary tract obstructions or neurological dysfunctions of the sphincter. Conclusions can be drawn about causes of pain, or diagnoses can be made, from the resulting diagrams and characteristic values (V(t)/Vmax/t).

SUMMARY

In order to perform this function, weighing concepts of very different designs are currently used. Essentially, the urine is always diverted into a collecting vessel, which stands on sensitive scales. By reading out the measured mass over time and calculating the volume over the density, a flow diagram can be produced. Many patents are concerned with optimizing this weighing principle in order to eliminate parameters which interfere with the measurement. Examples which may be mentioned here include DE 19 61 33 06 C2, GB 24 37 549 A, DE 300 78 55 C2 and EP 2 564 778 B1.

EP 2 564 778 B1 relates to a device and a method for urine flow measurement, which is to be designed to be as simple and maintenance-free as possible, so that it can also be used in a non-medical setting. The measurement principle consists of a measuring container which is arranged opposite a detector in such a manner that a displacement of the measuring container relative to the detector is detectable as a measure of the volume of urine collected in the measuring container. The displacement of the measuring container is here caused by gravity, which acts on the collected urine.

In practice, the use of scales as the means of acquiring measured values is frequently a problem. In order to ensure the validity of the measured values provided by the sensitive measuring means, the scales must regularly be calibrated. This leads to costs and downtimes of the measuring device for uroflowmetry. Also, there is a risk, in the daily routine of surgeries and hospitals, that the measuring means will be damaged by inappropriate handling—in the worst case, the validity of the measured values is then no longer guaranteed.

Accordingly, the disclosure is based on the object of eliminating the disadvantages of the prior art and providing an apparatus for measuring a flow of a fluid in dependence on time, in particular a urine flow, which is extremely robust, is simple to use and reliably provides valid measurement results.

This object is achieved by the apparatus as described herein. The use of the apparatus for measuring a urine flow per unit time is further described.

The present disclosure relates to an apparatus for measuring a flow of a fluid in dependence on time, in particular a urine flow.

The fluid, the flow of which is measured preferably has a density of from 0.95 to 1.05 g/ml, a temperature of from 10 to 40° C. and a dynamic viscosity of from 0.6 to 1.5 mPa*s. The fluid is particularly preferably urine or a urine/water mixture having a density of from 1.00 to 1.05 g/ml, a temperature of from 10 to 40° C. and a dynamic viscosity of from 0.6 to 1.5 mPa*s.

The apparatus according to the disclosure makes it possible in particular to measure the flow of volume flows of fluids of from 180 ml/min to 4200 ml/min.

According to the disclosure, the apparatus comprises an intake funnel;

a hose;

an ultrasonic flow sensor; and an overflow.

The purpose of the intake funnel is to catch all the fluid, in particular the urine, and divert it into the hose connected thereto. Its shape affects whether vortices form in the hose, which can impair the measurement. Intake funnels are known per se from the prior art; they have a part which extends conically and merges into an outflow portion. An intake funnel suitable for the apparatus according to the disclosure has a diameter of the opening of the conical part of between 5 cm and 30 cm.

In one embodiment of the present disclosure, the intake funnel has concentric flow breakers which taper to the outflow portion, and/or has a bent outflow portion. At the outflow portion, a first end of a hose is connected to the intake funnel.

If the intake funnel has concentric flow breakers tapering to the outflow portion, these can be arranged in the form of webs of quadrangular or circular cross section on the conical faces of the intake funnel. A maximum number of flow breakers in the intake funnel is not to be defined. In one embodiment of the disclosure, the intake funnel has 1, 2, 3, 4, 5, 6, 7, 8, 9 or 10 flow breakers. Vortex formation can also effectively be prevented by a surface that is rippled towards the centre.

If the intake funnel has a bent outflow portion, the axis of the bent outflow portion of the intake funnel deviates from the axis of the conical part of the intake funnel. Any vortices that may occur are thus reliably broken up. The formation of a thin air column within the vortex is prevented.

In a further embodiment of the present disclosure, the intake funnel has a mesh structure in the outflow portion of the funnel. That is to say, the mesh structure is arranged in the intake funnel before the connected hose.

The described embodiments of the intake funnel are suitable for preventing disruptive vortex formation.

According to the disclosure, a first end of the hose is connected to the intake funnel, as already described. This connection can be established simply by pulling the hose over the funnel outlet or vice versa, as well as by clamping the hose to the funnel outlet by means of a hose clamp. The diameter of the outflow portion is therefore such that the first end of the hose can correspondingly be connected with it.

The intake funnel is to comprise a material or consist of a material which ensures a smooth surface of the intake funnel and is resistant to cleaning chemicals. The intake funnel can therefore comprise materials or be produced from materials which are contained in the group comprising ceramics, enamel, stainless steel and aluminium. In one embodiment, the intake funnel comprises an inert plastics material selected from the group comprising polyethylene (PE), polypropylene (PP), polyethylene terephthalate (PET), polyamide (PA), acrylonitrile-butadiene-styrene (ABS), polytetrafluoroethylene (PTFE). In one embodiment of the disclosure, only the surfaces that come into contact with the fluid comprise the described materials.

A first end of the hose is arranged at the intake funnel, and the second end of the hose is connected according to the disclosure to the overflow. The connection to the overflow can be established simply by pulling the hose over the overflow or vice versa, as well as by clamping the hose to the overflow by means of a hose clamp. According to the disclosure, the hose runs in a U-shape. In a U-shape describes a profile of the hose in which the first and second ends of the hose are bent upwards in the vertical direction. The bend does not necessarily have to be 90°. However, the two ends of the hose are arranged higher than its middle, which corresponds to a U-shape. The first and second ends of the hose do not have to be at the same height.

According to the disclosure, the ultrasonic flow sensor is further arranged on the hose. The ultrasonic flow sensor is particularly preferably clamped to the hose. This is possible by means of a so-called clamp-on flow sensor.

In a preferred embodiment, the length of hose is kept straight in one embodiment before it enters the sensor over a length of at least 10×ID upstream of the ultrasonic flow sensor and over a length of at least 5×ID downstream of the ultrasonic flow sensor. In this context, kept straight means that the straight length of hose is formed at an angle of from 0° to ±30° relative to the horizontal. This straight form ensures that disruptions to the flow profile are avoided and a reliable measurement is thus made possible. ID denotes the inside diameter of the hose.

According to the disclosure, an ultrasonic flow sensor is used for carrying out the flow measurement. This is particularly suitable owing to its non-invasive mode of functioning. There is no other measuring method which could carry out a flow measurement non-invasively with an accuracy of up to 2% or better. An initial adjustment of the sensor or automatic adaptation to the hose parameters is advantageous in order to achieve the desired accuracy. Such a calibration is advantageously necessary only once, because the measurement technique known from the prior art is sufficiently robust in this area.

In one embodiment of the present disclosure, the ultrasonic flow sensor is distinguished in particular in that it is clamped to the hose filled completely with fluid without a coupling means. Ultrasonic signals with a frequency of between 1 MHz and 4 MHz are preferably used in the measurement. The flow of the fluid can thus be measured non-invasively, that is to say without contact with the fluid in the hose, with an accuracy of ±15%, preferably of ±5%, particularly preferably of ±2%.

In a further embodiment of the present disclosure, the ultrasonic flow sensor has at least one analogue and/or digital interface. Analogue interfaces can be, for example, a flow output, frequency output, PWM or the like. Digital interfaces permit serial communication by way of a standardized or proprietary protocol. By way of this at least one interface, the measured values can be transmitted to a unit for evaluation. A unit for evaluation is, for example, a PC or the like. The measured values can be processed further in this unit.

In one embodiment, the present disclosure has an interface that enables wireless remote transmission of the measurement data. This can be implemented via a WLAN interface and/or an interface to a mobile radio network or similar. Advantageously, the measurement data can thus be transmitted remotely and the apparatus according to the present disclosure can also be used independently outside medical practices, for example at a patient's home or in a care facility. The measurement data could then be sent automatically to the physician at any time, regardless of location, and analysed by the physician.

In a preferred embodiment of the present disclosure, the apparatus according to the disclosure further comprises a battery or accumulator. This supplies the apparatus with the necessary power. The apparatus according to the disclosure can then advantageously be operated autonomously, i.e. independently of a stationary power source.

A hose that is suitable for the apparatus according to the disclosure must be so designed that a flow of up to 4 l/min (in the case of healthy individuals in early adulthood) can pass through without appreciable backing up. Backing up would lead to a delay in measuring the flow and thus to falsification of the result. However, the absolute measurement accuracy of ultrasonic clamp-on flow sensors decreases as the inside diameter of the hose increases. The reason for this is that the sensor only measures a flow velocity, which is converted into a volume flow by multiplication by a factor. Consequently, small flows would best be measured using thin hoses, because the flow velocity in the case of small flows is higher here than in the case of thicker hoses. In the case of thicker hoses, the measuring effect and as a result also the measurement accuracy thus decreases while the volume flow remains the same. For these reasons, an optimum must be found between a thick hose (real representation of high flows) and a thin hose (high accuracy in the case of low flows).

It has been shown that in particular hoses having an inside diameter (ID) in the region of 3/8"±50%, preferably in the region of 3/8"±25%, particularly preferably of 3/8", meet these requirements and are therefore used in an embodiment of the present disclosure.

In one embodiment of the disclosure, the hose further has a wall thickness in the region of 3/32"±50%, preferably in the region of 3/32"±25%, particularly preferably of 3/32". These wall thicknesses have been found to be advantageous in order to obtain as high a measurement accuracy as possible.

In one embodiment the hose is a polymer hose. Preferably a flexible polymer hose. Flexible in this context means that the hose can be bent into the desired U-shape by the application of purely mechanical force. In a particularly preferred embodiment the hose comprises a material selected from the group comprising silicone and PVC.

In one embodiment of the present disclosure, the apparatus further comprises a discharge valve, which is arranged on the hose between the ultrasonic flow sensor and the overflow. It is preferably situated at the deepest point of the hose arranged in a U-shape. It allows the system to be emptied if required, for example at the end of a working day, after a measuring operation or for maintenance of the apparatus. The discharge valve can be arranged upstream or downstream of the ultrasonic flow sensor. It is advantageous if the discharge valve is not arranged too close to the measurement point of the ultrasonic flow sensor. In one embodiment of the apparatus according to the disclosure, the distance between the ultrasonic flow sensor and the discharge valve is at least 10 times the inside diameter of the hose. The distance is measured between the edge of the ultrasonic flow sensor that faces the discharge valve and the edge of the discharge valve that faces the ultrasonic flow sensor.

According to the disclosure, the apparatus comprises an overflow. The overflow has a significant influence on the accuracy of the measuring system. It is to be ensured that a suction effect by the outflowing medium on the medium situated in the hose is suppressed. In one embodiment of the present disclosure, the second end of the hose therefore has a vertical, upwardly directed outlet opening in the overflow. This configuration suppresses a suction effect, which cannot be ensured in the case of a horizontal or downwardly directed hose outlet.

In a further embodiment, the apparatus further comprises a collecting container, which is arranged downstream of the overflow. In an alternative embodiment, the overflow opens into a drain. In both embodiments, it is ensured that the fluid which leaves the hose at the overflow does not run down the hose. This is to be avoided for hygiene reasons. Moreover, proper disposal of the fluid is made possible in this way.

The collecting container can be part of an device which wholly or partially encloses the intake funnel, the hose, the ultrasonic flow sensor and the overflow, or it can also be loosely connected to the overflow. If the collecting container is loosely connected to the overflow, the fluid collected therein can advantageously be supplied to further investigations. By the device wholly or partially enclosing the intake funnel, the hose, the ultrasonic flow sensor and the overflow is meant an enclosure enclosing of the components, resulting in a compact form of the device according to the disclosure. By compact form is meant that the individual components are arranged in the enclosing in as space-saving a manner as possible. This allows the apparatus to be easily moved by a user. Furthermore, when used in care facilities or at home, transportation is easy and storage of the apparatus according to the disclosure when not in use also takes up little space.

In one embodiment, therefore, parts of the apparatus or the entire apparatus have an enclosure.

In a further embodiment, the apparatus further comprises a chair structure or a urinal, wherein the chair structure or the urinal is connected to the intake funnel, or the intake funnel is formed by the chair structure or the urinal, or the mentioned apparatus in a compact structural form is suspended in a toilet. In these embodiments, the collecting container can be formed, for example, by the urinal or the chair structure. In this case, the collecting container wholly or partially encloses the intake funnel, the hose, the ultrasonic flow sensor and the overflow of the apparatus.

A chair structure can be, for example, a commercially available commode, as is used in the care sector and in clinics.

The use of the apparatus for measuring a urine flow per unit time is further described. The apparatus according to the disclosure is suitable in particular for use in urological surgeries or clinics. Home use is also possible with the apparatus according to the disclosure.

The measurement of a fluid flow, in particular of a urine flow, with the apparatus according to the disclosure is found to be extremely robust. The use of an ultrasonic flow sensor instead of scales eliminates the deficiencies mentioned in the prior art. In particular the use of a non-invasive ultrasonic flow sensor improves the handling and the robustness of the measurement considerably. A clamp-on flow sensor is capable of measuring the volume flow of the fluid stream, in particular of a urine stream in the hose, through the wall of a plastics hose (e.g. silicone, PVC or similar). Ultrasound-based technology measures even very small flows reliably and with high precision. A setup adapted for the measuring method ensures valid and accurate measurement results at all times. Re-calibration of the flow sensor is not necessary because the clamp-on sensor system is free from wear and is robust. The clamping of such a sensor to a hose line and also the use thereof is possible for inexperienced staff without appreciable training.

BRIEF DESCRIPTION OF THE FIGURES

The disclosure will be explained in greater detail below by means of 6 figures and an example.

DETAILED DESCRIPTION

Figure 1:
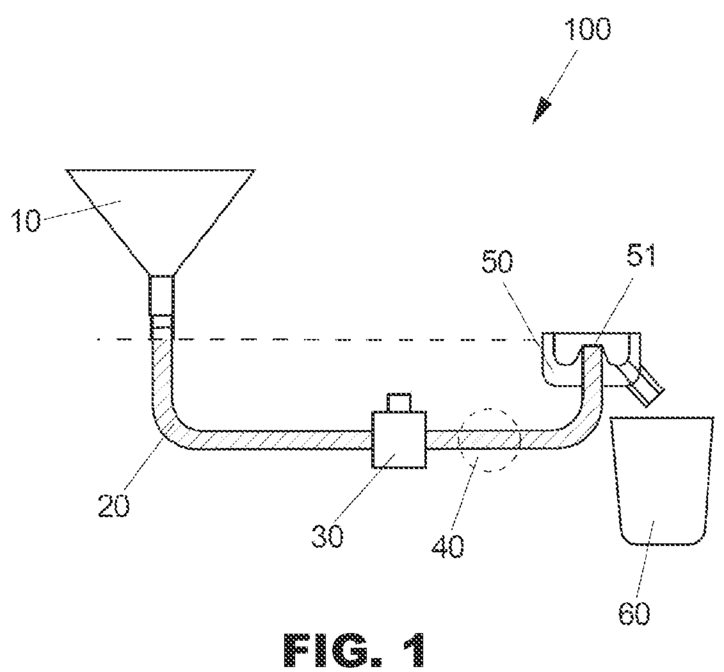
FIG. 1 shows a setup of the apparatus according to the disclosure.

FIG. 1 shows a setup of the apparatus 100 according to the disclosure. The intake funnel 10 is connected to a first end of the hose 20. The ultrasonic flow sensor 30 is clamped to the hose 20. Downstream of the ultrasonic flow sensor 30 there is arranged a discharge valve 40, with which the apparatus 100 can be emptied if required. The second end of the hose opens into the overflow 50. The second end of the hose has a vertical, upwardly directed outlet opening 51 in the overflow. The upwardly directed outlet opening is formed by the second end of the hose, which is directed upwards. The apparatus 100 additionally has a collecting container 60 in the form of a vessel.

Figure 2:
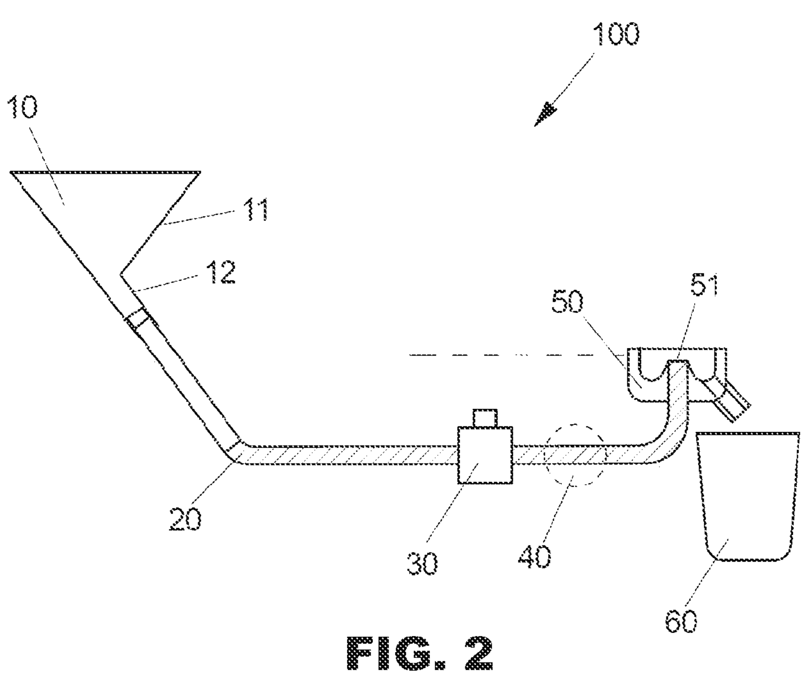
FIG. 2 shows a setup of the apparatus according to the disclosure with a bent intake funnel.

FIG. 2 shows a further embodiment of the apparatus 100 according to the disclosure. The apparatus 100 has the same setup as described in relation to FIG. 1. Only the intake funnel 10 is configured differently than in FIG. 1. The intake funnel 10 has a bent outflow portion 12, so that the axis of the bent outflow portion 12 of the intake funnel deviates from the axis of the conical part of the intake funnel 11. The axes are shown by broken lines in the figure.

Figure 3A:
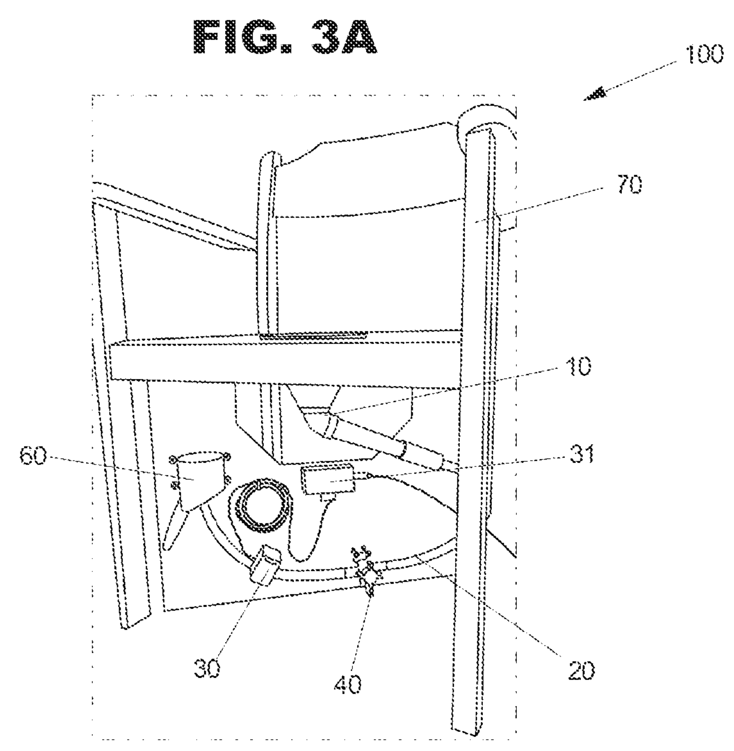
FIGS. 3(A) and (B) show a setup of the apparatus according to the disclosure with a chair structure.
Figure 3B:
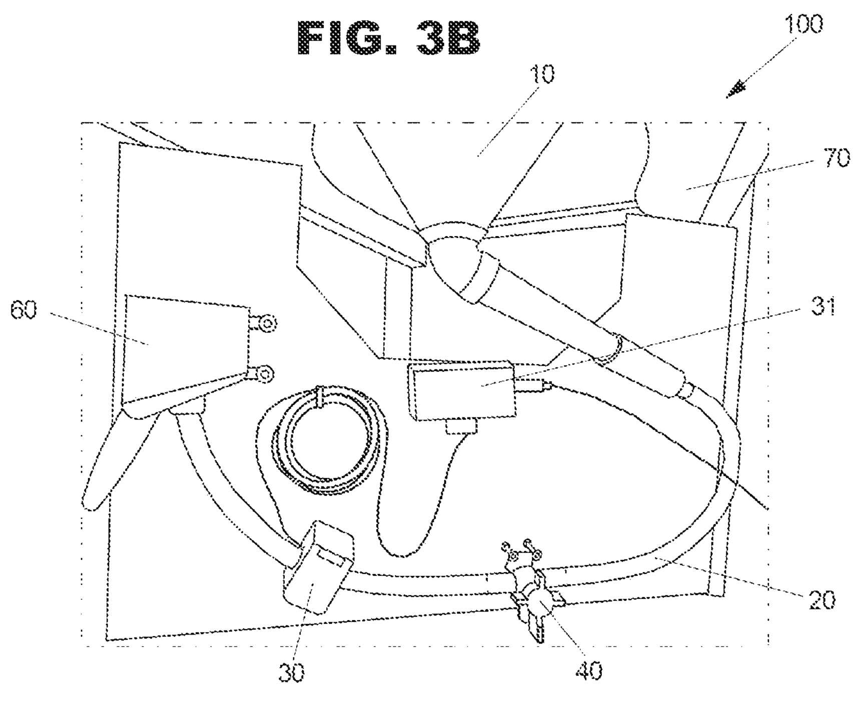

FIG. 3(A) shows a setup of the apparatus 100 according to the disclosure with a chair structure 70. FIG. 3(B) shows an enlarged detail of the setup of the apparatus 100 according to the disclosure. The chair structure 70 is a commode as is known from the specialized trade for sanitation products. The further components of the apparatus are mounted beneath the commode. The intake funnel 10 is arranged in the opening in the seat area of the commode. The intake funnel 10 is connected to the first end of the hose 20. The outlet valve 40 and the ultrasonic flow sensor 30 are arranged on the hose 20. The ultrasonic flow sensor 30 is connected to a data converter 31, which in turn permits a connection to a PC (not shown). The second end of the hose 20 opens into the overflow 60.

Figure 7:
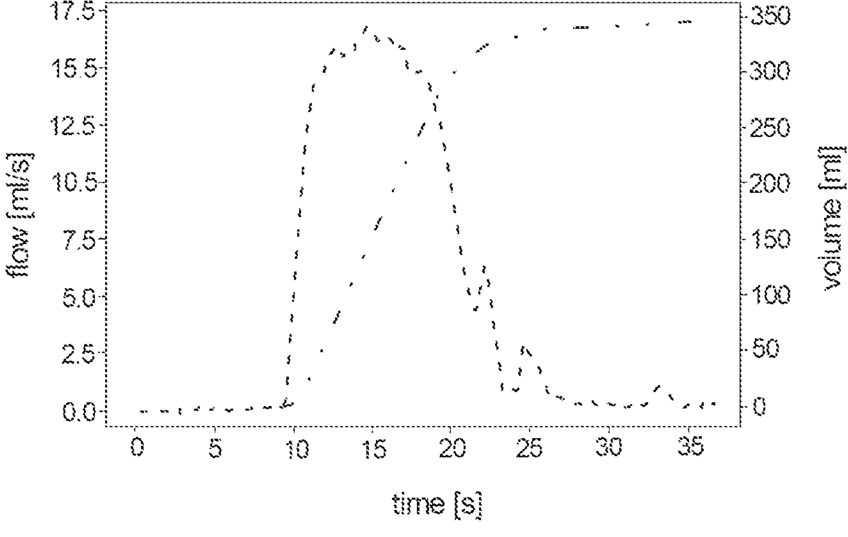
FIG. 7 shows a measurement of volume flow which changes over time.

FIG. 7 shows the measurement results of a measurement of a volume flow which changes over time. The curve that rises and falls again shows the flow in ml/s over time. The curve that rises and then runs constantly shows the measured total volume in dependence on time.

Figure 4A:
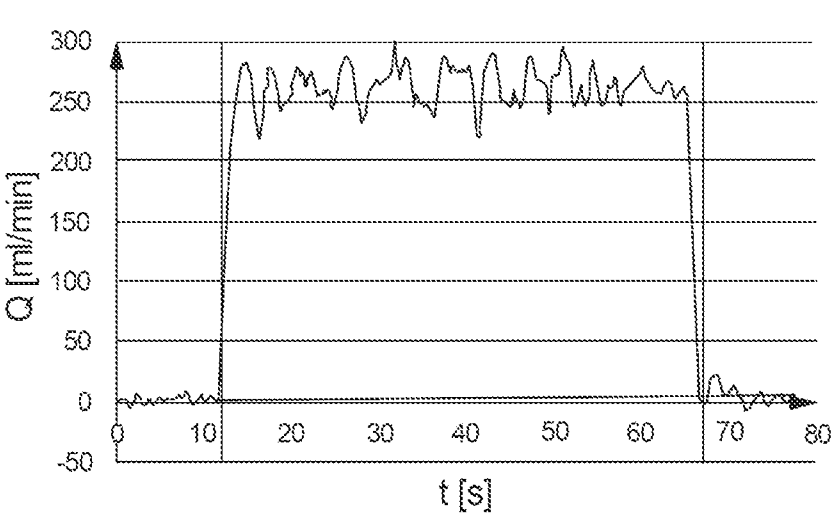
FIGS. 4(A) and (B) show the volume flow over time for two different volume flows.
Figure 4B:
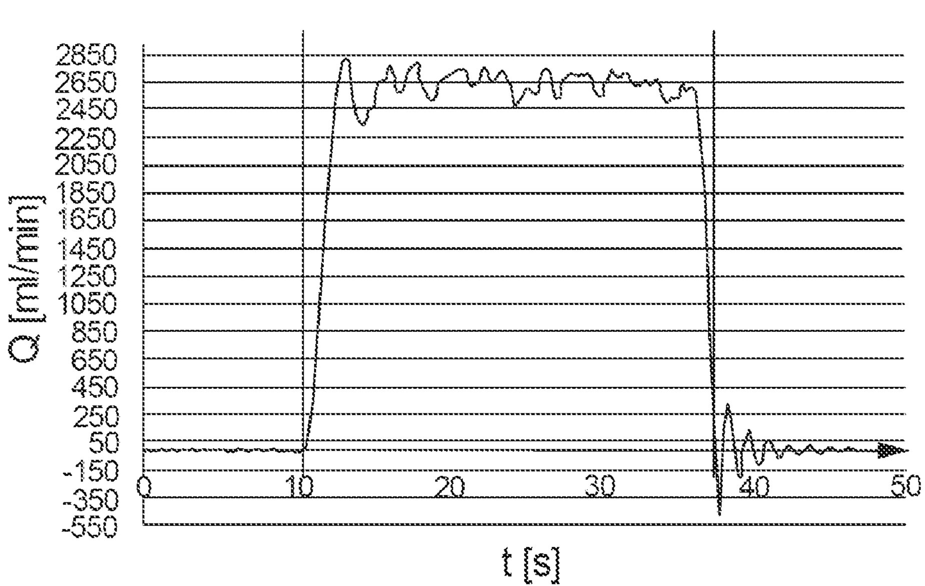
Figure 5A:
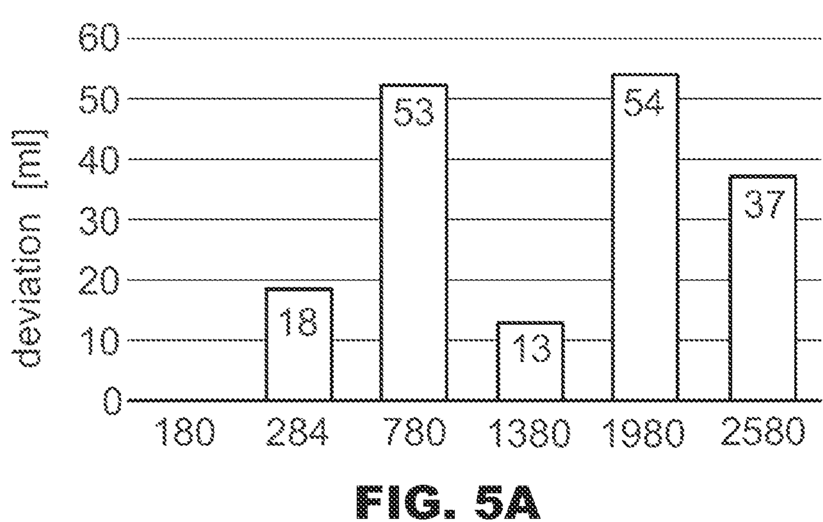
FIG. 5(A) shows the absolute deviation of the measured values of a measurement using the apparatus according to the disclosure relative to a weighing measurement; (B) shows the relative deviations of the measurement results.
Figure 5B:
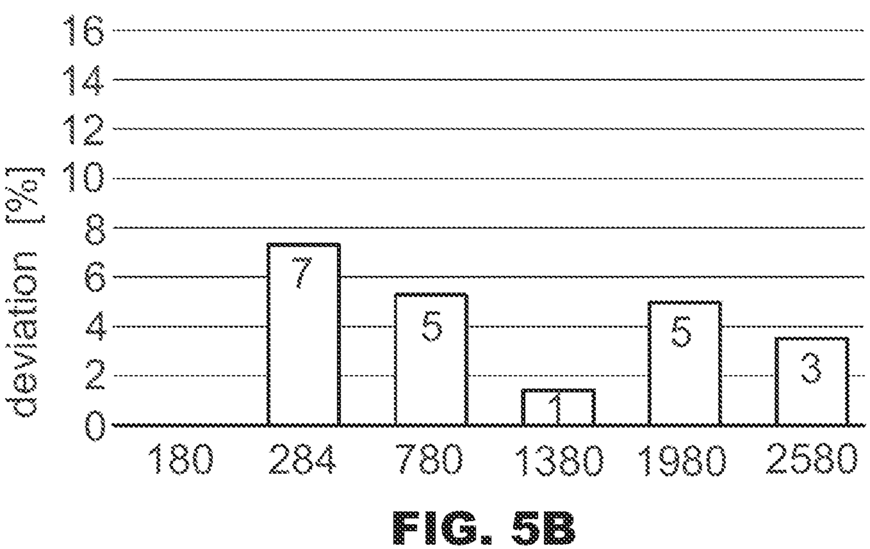
Figure 6A:
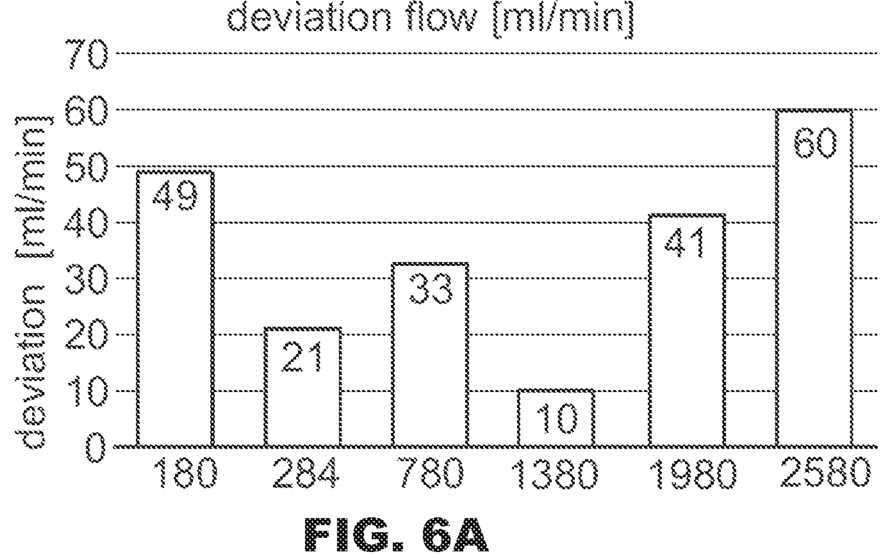
FIG. 6(A) shows the absolute deviation of the measured values of a measurement using the apparatus according to the disclosure relative to a weighing measurement for different volume flows; (B) shows the relative deviation of the measurement results.
Figure 6B:
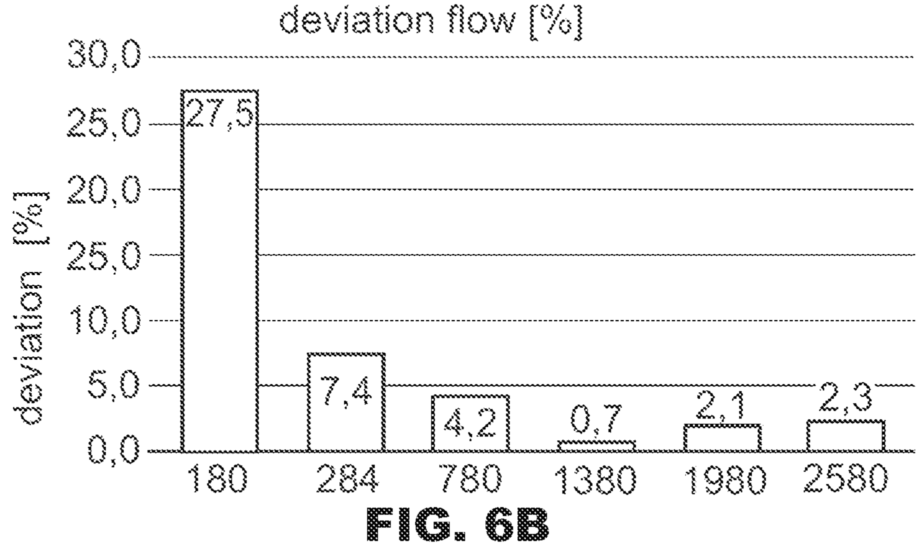

FIGS. 4 to 6 will be explained in greater detail in connection with the exemplary embodiment.

Exemplary Embodiment 1

In order to validate the apparatus according to the disclosure, comparison measurements were carried out. To this end, a constant volume flow (water, 23° C.) was generated by means of a pump and directed by means of a hose into the funnel. The hose was not kept still, but the intake position was constantly varied slightly in order to simulate a urination process. Defined flows of between 180 ml/min and 2560 ml/min were generated. A reference sensor measured the flow that was generated before it exited into the apparatus according to the disclosure. After passing through the apparatus according to the disclosure, the water was collected in a collecting container for weighing.

FIGS. 4(A) and (B) shows a measurement signal of the ultrasonic flow sensor for a volume flow of 180 ml/min (FIG. 4(A)) and for a volume flow of 2560 ml/min (FIG. 4 (B)). After the volume flow is stopped, a small post-oscillation of the fluid column is to be observed in the measurement signal in particular in the case of higher flows. The measurement results for the different constant volume flows are shown in FIGS. 5 and 6. In the case of low flows (180 ml/min and 284 ml/min), the measurements show a slightly higher deviation of the flow measurement from the actual flow. In the case of higher flows, however, the measurement error falls constantly to less than 5% (see FIG. 6). The volumes can also reliably be reproduced with the apparatus according to the disclosure—the errors here behave similarly to the case of the flow measurement, which was also to be expected due to the direct relationship between the flow and the volume (see FIG. 5). In FIGS. 5 and 6, the absolute deviation of the measured values of a measurement using the apparatus according to the disclosure relative to a weighing measurement is in each case shown in Figure (A), and the relative deviation of the measurement results is shown in Figure (B).

By means of the apparatus according to the disclosure, a reliable evaluation of a urination process is therefore possible. The measurement error in the case of low volume flows (≤284 ml/min) is still sufficient to make a correct diagnosis in the medical sense. For flows in higher volume flows (>284 ml/min), the error, at <5%, is substantially smaller. The reproduction of a meaningful flow characteristic curve is also possible in this range.

LIST OF REFERENCE SIGNS

10 intake funnel
11 part of the intake funnel
12 outflow portion of the intake funnel
20 hose
30 ultrasonic flow sensor
31 data converter
40 discharge valve
50 overflow
51 upwardly directed outlet opening
60 collecting container
70 chair structure
100 apparatus

The invention claimed is:

1. An apparatus for measuring a flow of a fluid in dependence on time, in particular a urine flow, comprising an intake funnel;
a hose;
an ultrasonic flow sensor;
an overflow;
wherein
a first end of the hose is connected to the intake funnel and a second end of the hose is connected to the overflow;
the ultrasonic flow sensor is arranged on the hose;
the hose is U-shaped;
wherein the intake funnel has a mesh structure in an outflow portion of the intake funnel before the hose; and
wherein the second end of the hose has a vertical, upwardly directed outlet opening in the overflow.

2. The apparatus according to claim 1, wherein the hose runs straight over a length of at least 10 times an inside diameter of the hose upstream of the ultrasonic flow sensor and over a length of at least 5 times the inside diameter of the hose downstream of the ultrasonic flow sensor.

3. The apparatus according to claim 1, wherein the hose is a polymer hose.

4. The apparatus according to claim 1, wherein the ultrasonic flow sensor is clamped to the hose without a coupling.

5. The apparatus according to claim 1, wherein the apparatus further comprises a discharge valve, which is arranged on the hose between the ultrasonic flow sensor and the overflow.

6. The apparatus according to claim 1, wherein the apparatus further comprises a collecting container, which is arranged downstream of the overflow.

7. The apparatus according to claim 1, wherein the intake funnel has a bent outflow portion.

8. The apparatus according to claim 1, wherein the apparatus further comprises a battery or accumulator.

9. The apparatus according to claim 1, wherein at least parts of the apparatus have an enclosure.

10. The apparatus according to claim 1, wherein the apparatus further has a chair structure or a urinal, wherein the chair structure or the urinal is connected to the intake funnel, or the intake funnel is formed by the chair structure or the urinal, or the apparatus in a compact structural form is suspended in a toilet.

* * * * *